United States Patent [19]

Morgan et al.

[11] Patent Number: 5,009,652

[45] Date of Patent: Apr. 23, 1991

[54] MEDICAL SPONGES AND WIPES WITH A BARRIER IMPERMEABLE TO INFECTIOUS AGENTS

[76] Inventors: Cheryle I. Morgan, 6562 Patrick Dr., Dallas, Tex. 75214; Millard M. Judy, 5740 Palo Pinto Dr., Dallas, Tex. 75206

[21] Appl. No.: 109,571

[22] Filed: Oct. 16, 1987

[51] Int. Cl.⁵ ............................................. A61F 13/15
[52] U.S. Cl. ................................ 604/385.1; 604/378
[58] Field of Search ............... 604/289, 290, 293, 303, 604/304, 308, 312, 358, 360, 378, 1-3, 385; 128/155, 851, 854, 830, 832, 833, 837, 839, 841; 15/244.1-244.4, 209 D; 401/130, 132, 137, 135, 139

[56] References Cited

U.S. PATENT DOCUMENTS

| | | | |
|---|---|---|---|
| 814,408 | 3/1906 | Steele | 604/289 |
| 1,565,775 | 12/1925 | Bash | 15/244.4 |
| 1,723,520 | 8/1929 | Pintel | 15/209 D |
| 2,007,238 | 7/1935 | Anderson | 15/244.4 |
| 2,789,301 | 4/1957 | Harvey | 401/130 |
| 2,961,677 | 11/1960 | Zecchini | 15/244.4 |
| 2,999,265 | 9/1961 | Duane et al. | 604/289 |
| 3,180,335 | 4/1965 | Duncan et al. | 604/370 |
| 3,363,625 | 1/1968 | Govis | 604/289 |
| 3,386,793 | 6/1968 | Stanton | 401/132 |
| 3,559,650 | 2/1971 | Larson | 604/373 |
| 3,654,064 | 4/1972 | Laumann | 604/370 |
| 3,779,246 | 12/1973 | Mesek et al. | 604/370 |
| 4,140,409 | 2/1979 | De Vries | 604/289 |
| 4,216,774 | 8/1980 | Graber | 604/372 |
| 4,300,544 | 11/1981 | Rudel | 128/837 |
| 4,519,795 | 5/1985 | Hitchcock et al. | 604/289 |
| 4,524,767 | 6/1985 | Glassman | 128/854 |
| 4,575,891 | 3/1986 | Valente | 604/289 |
| 4,701,168 | 10/1987 | Gammons | 604/1 |

FOREIGN PATENT DOCUMENTS

| | | | |
|---|---|---|---|
| 0161204 | 11/1985 | European Pat. Off. | 604/304 |
| 0780443 | 7/1957 | United Kingdom | 604/289 |
| 0976630 | 12/1964 | United Kingdom | 604/308 |

*Primary Examiner*—C. Fred Rosenbaum
*Assistant Examiner*—Sharon Rose
*Attorney, Agent, or Firm*—Johnson & Gibbs

[57] ABSTRACT

A disposable laminated medical sponge contains a thin sheet, having a top side and a bottom side, that is impermeable to infectious agents as well as nonwettable by water and a layer of absorbent material having an area that is smaller than that of the impermeable sheet, and one surface of which is secured to at least one side of the impermeable sheet. The peripheral edges of the absorbent layer are spaced inwardly from the peripheral edges of the impermeable sheet, providing a surrounding rim that consists of impermeable sheet alone. Any liquid on the layer of absorbent material cannot travel through and over the peripheral edges of the impermeable sheet to reach the opposite side of the impermeable sheet. Consequently, any infectious agents such as viruses that might be present in the body fluids cannot be transmitted from the absorbent material to the opposite side of the medical sponge that is being held by a healthcare worker. An alternate embodiment shows a laminated medical sponge further containing an integral peripheral ridge surrounding the completely peripheral edges of at least one side of the impermeable sheet providing a peripheral moat of the impermeable sheet alone.

5 Claims, 2 Drawing Sheets

MEDICAL SPONGES AND WIPES WITH A BARRIER IMPERMEABLE TO INFECTIOUS AGENTS

BACKGROUND OF THE INVENTION

The present invention relates to disposable medical sponges or wipes which are impermeable to infectious agents, such as the virus that causes Acquired Immune Deficiency Syndrome (AIDS).

Since the beginning of the century, designers of disposable absorbent articles have always been, and still are, confronted with the problem of having liquid migrating laterally on one side of the absorbent article and seeping over the peripheral edges to reach the opposite side of the article. Yet, there is so far no satisfactory solution to this problem.

As will be discussed later, there is a need of having disposable medical sponges or wipes that will not allow the seepage of patient's body fluids and pathogens through the sponges or wipes to infect a health-care worker. It is well documented that body fluids from an infected person do carry with them infectious agents, such as the virus that causes the deadly AIDS. A "leaky" medical sponge or wipe can also expose the patient to possible contamination by an infected health-care worker. A simple impermeable membrane interposed to the medical sponge or wipe will not completely solve the problem. Absorbed body fluids, together with any infectious agents that might be present therein, can still migrate laterally on the absorbent side of the sponge and seep around and over peripheral edges from this absorbent side to the opposite non-absorbent side which is being held by a health-care worker. A desirable medical sponge or wipe must additionally have wet strength, namely, they must not disintegrate when totally soaked in liquids, such as body fluids or a solution of antiseptics.

Disposable absorbent articles, such as diapers, underpads, surgical dressings, medical sponges, wipes, and cosmetic squares, are well known in the prior art. These articles can be broadly divided into two classes: those with a water impermeable sheet and those without a water impermeable sheet.

Articles containing a liquid impermeable sheet have the same general structure. They usually contain an absorbent medium enclosed by a liquid permeable top sheet and a liquid impermeable backsheet. The top sheet is the sheet in direct contact with the skin of the user. Its function is to draw the waste away from the contacting skin into the absorbent medium where the waste is retained. The top sheet reduces the direct contact of the waste with the skin. The water impermeable backsheet prevents the absorbed waste from leaking out of the absorbent article and soiling the surrounding area. The prior art is replete with variations of these general structure. Diapers, sanitary napkins, under pads, are some of the examples.

Another broad class of disposable articles include medical sponges, wipes, gauze, and cosmetic squares. Typically, they contain a layer of porous absorbent material only. There is no separate top sheet, nor is there a layer of material impermeable to water. Consequently, there is not much variation in the overall structure of such a disposable article. Medical sponges or wipes are used to wipe blood or other body fluids from the body of a patient. They are also used to apply pressure or solutions of antiseptic to the body of the patient after, or in preparation for, an injection or a venipuncture procedure.

U.S. Pat. No. 1,843,037 to Mathey discloses a relatively inexpensive sanitary napkin that does not readily leak and stain the clothing. The article contains a separator element such as a thin sheet of lightly waxed crepe cellulose paper. There is an absorbent pad on either side of this separator which extends flush with the marginal walls of the pad. The separator retards fluid flow to the next layer of pad until complete diffusion has ensued in the top pad. Afterward, the separator permits seepage of fluid through it to the bottom pad where the same diffusion action occurs due to the presence of the garment protection. The separator does not completely stop the penetration of fluids, rather it simply retards the seepage of fluids from one pad to the other.

U.S. Pat. No. 4,321,924 to Ahr discloses a bordered disposable absorbent article. The article is for absorbing liquids, such as menstrual discharges. The disposable absorbent article contains an absorbent core encased between a liquid permeable top sheet and a liquid impermeable backsheet. The article is further provided with a thin flexible border which encircles the absorbent core. The border may be formed by extending the back sheet and the topsheet, which is liquid permeable, beyond the absorbent core and affixing the topsheet to the backsheet along two liquid impermeable seams. An inward seam is positioned to the core and an outward seam is positioned in spaced relation to the inward seam, thus forming an enclosed channel which encircles the absorbent core. The enclosed channel is bound by the two liquid impervious seams. To the top of the enclosed channel is the liquid permeable topsheet, and to the bottom of the enclosed channel is the liquid impermeable backsheet. The topsheet and the backsheet are affixed to one another by the inward seam on the inside, and they are affixed to one another at the outer periphery by the outward seam. Hence, the liquid permeable topsheet is flush with the liquid impermeable backsheet at the outward seam. Seepage from top to bottom sheet is not reliably retarded, however.

U.S. Pat. No. 3,779,246 to Mesek and Repke describes a disposable diaper. The disposable article contains an absorbent fibrous pad enclosed by a fibrous facing layer and a water impervious sheet which, in turn, is enclosed by a fibrous outermost layer. The fibrous outermost layer is incorporated to increase the stability and functionality of the diaper. Again, the peripheral edges of all three layers, namely, the fibrous facing layer, the water impervious sheet, and the fibrous outermost layer, are all contiguous and flush to one another.

A U.S. patent issued to Puletti and Decowski under U.S. Pat. No. 4,627,847 describes a hot melt adhesive waste barrier. The invention relates to waste barriers for use in disposable absorbent articles such as diapers, sanitary napkins, bed pads, and the like. The patent describes the creation of a self-adhesive, leakage-resistant, waste barrier on the nonwoven topsheet by coating or depositing a hot melt adhesive to a portion of this topsheet, thus creating a liquid impermeable film. The nonwoven topsheet is in contact with at least one surface of an absorbent core.

U.S. Pat. No. 3,523,536 to Ruffo discloses absorbent fibrous pads which have an absorbent core enveloped in a liquid permeable coverings. The core is composed of predominately short fibers intermixed in a dry state with long fibers to form a heterogeneous mixture in which the long fibers serve to stabilize the short fibers. The liquid permeable coverings, the absorbent core and a layer of synthetic resin film are sealed at their peripheries by means of heat embossing elements.

U.S. Pat. No. 4,338,371 to Dawn and Correale teaches a multilayer absorbent product to absorb fluids. The laminated article is enclosed on the top by a water pervious facing layer for contacting the skin, and on the bottom by a liquid impermeable layer. This liquid impermeable layer, however, is permeable to gas. Immediately under the top water pervious facing layer is the first fibrous wicking layer. Under this wicking layer is the first absorbent mass defined by an inner and an outer layers of wicking material. Under these is another absorbent mass again defined by an inner and an outer layer of a water pervious wicking material. On the bottom is the layer that is impermeable to liquid but is permeable to gas.

A U.S. Pat. No. 3,901,240 issued to Hoey discloses an absorbent article having a top layer of a crushed polymer latex foam either bonded to a non-woven absorbent layer, which is bonded to an absorbent layer, or bonded directly to the absorbent layer. The latter layer is, in turn, bonded either to a flexible, liquid impermeable bottom layer or to a woven or non-woven gauze. The patent describes the procedure for producing such a permeable polymeric liner on absorbent pads.

A patent issued to Hirsch, U.S. Pat. No. 4,477,256, shows a surgical sponge for blunt dissection embodying an X-ray opaque material. The sponge consists of elongated strip of absorbent material such as woven cotton or the like rolled to form a cylindrical structure. The outer layer of the roll is adhesively secured to the roll to prevent unwinding. A radiation opaque material, such as barium sulfate, is contained within the sponge and is intermixed with the adhesive.

U.S. Pat. No. 4,216,774 issued to Graber teaches a reusable, washable incontinent care medical pad. The pad includes a top layer of soft, nonabrasive material, a second inner layer of maximum absorbency and softness material, a third inner layer of structural support material for stitching to the first and second layers. A fourth layer of water impermeable material is then aligned and stitched together with all other layers.

U.S. Pat. No. 3,777,759 issued to Oehmke and Ofstead discloses an enzyme-dispersible bandage. The bandage is a disposable multi-ply pad for contacting the body and absorbing body wastes. The article consists of multiple plys of non-woven, fibrous material of good dry-strength and wet-strength. The wet-strength is being conferred on the article by a binder which is essentially unaffected over periods of several hours by aqueous body waste, but which is rapidly degraded by exposure to aqueous media containing certain enzymes. The whole pad can be readily dispersed and is disposable in domestic waste disposal systems by the addition of enzymes to the disposal receptacle together with the used pad.

Larson in U.S. Pat. No. 3,559,650 teaches a disposable sanitary pad having a disposable absorbent pad on the upper side and a disposable backing of paper or similar material on the under side, with a thin flexible layer liquid-retarding material between the two. All layers have edges flush to one another. Liquid from the pad cannot reach the backing to dissolve it, but liquid reaching the backing from its exposed side will disintegrate it so that the whole article can be disposed of in a toilet. The thin layer of liquid-retarding material cannot remain as a film without the support of the backing material, so that it, too, disintegrates when the backing material disintegrates.

U.S. Pat. No. 3,654,064 to Laumann discloses a waterdisintegratable sheet material. The coated paper is provided in sheet, roll or other physical form and shape which is water-repellent when wetted on either side. The article, however, readily disintegrates when both sides are wetted as when the entire sheet is immersed in water. An extremely thin layer of polyethylene covers a tissue paper which readily disintegrates in water. The polyethylene serves as a hold-out coating for a subsequent water-repellent coating such as a flexible wax layer to prevent the sinking of the wax layer into the tissue paper and rendering the paper water-insoluble and providing it with wet strength properties. A layer of uncoated sheet tissue paper is placed on top of the coated sheet. When wetted on one side, the sheet derives its strength from the bottom layer of paper which is kept dry and strong by the waterrepellent coating. The coating itself has no stretch properties and is very weak. When both top and bottom layers or papers are wetted, as when flushed in a toilet, the entire sheet tears and disintegrates since there remains nothing to support the thin, weak water-insoluble coating.

Although prior art references are replete with references for disposable absorbent articles, none teaches a design to totally prevent the seepage or migration of fluids from one side of the article to the opposite side of the article over the peripheral edges. The prior art references teach that these edges should hold the absorbent and nonabsorbent layers contiguously together in an abutting manner. Hence, liquids absorbed on one side to he article can migrate laterally and seep over the peripheral edges to reach the opposite side of the article. Additionally none teaches a design to prevent penetration of the barrier layer by viral pathogens, the smallest of the infectious agents.

Health-care workers are persons, including students and trainees, whose activities involve direct contact with patients or with human body fluids such as blood, saliva, semen, tears, vaginal secretions, cerebrospinal fluid, amniotic fluid, urine, breast milk, and anal mucus drainage. These health-care workers are at risk of exposure to infectious agents carried by patients on a routine and daily basis. Likewise, patients also run the risk of exposure to infectious agents from infected health-care workers. The term "infectious agents" as used here denotes bacteria, viruses, parasites, and other infectious microorganisms.

The increasing prevalence of AIDS among populations in the world increases the risk that health-care workers will be exposed to blood or other body fluids from patients with AIDS. About 5 to 10 million people from more than 80 countries are infected with this deadly disease. AIDS is caused by human immunodeficiency virus (HIV). To date, AIDS has proven invariably fatal. There is no effective treatment for the disease, nor is there a vaccine to prevent it. On the average, AIDS victims live about two years after the diagnosis. Because the disease has an undetermined period of incubation, a person unknowingly can carry the virus and spread the disease for years. Hence, transmission of disease may occur before the illness is recognizable. The method most frequently used to establish the presence of HIV is the detection of antiviral antibody. Yet, it is known that certain carriers of HIV may harbor the virus for an undetermined time before producing detectable antibodies. A significant proportion of "high risk" groups, such as gay men, illegal drug users, prostitutes, and hemophiliacs, are asymptomatic. This phenomenon suggests that the pool of individuals capable of transmitting the disease is significantly larger than the presently known number of diagnosed AIDS cases. Consequently, health-care workers must consider the blood and other body fluids from all patients as being potentially infective.

AIDS can be transmitted through sexual contact and exposure to infected blood or blood components and perinatally from mother to neonate. The virus, HIV, has been isolated from blood, semen, vaginal secretions, saliva, tears, breast milk, cerebrospinal fluid, amniotic fluid, and urine and is likely to be isolated from other body fluids, secretions, and excretions. So far, epidemiologic evidence has positively implicated blood, semen, vaginal secretions, and possibly breast milk in the transmission of the fatal disease.

A number of health-care workers have been reported to have acquired HIV infection through needlestick, exposure of mucous-membranes or of skin lesions to the blood or other body fluids of HIV-infected patients. The increased risk of a health-care worker to AIDS involves in part the exposure of his or her skin to HIV and the opportunity for HIV to gain access to within the body through cuts, or other skins lesions such as abrasions, scrapes, chapping of the skin or dermatitis. These "defects" on the skin compromise the normal function of the skin as the natural barrier against entry by infectious agents into the body. Viruses, because of their extremely small sizes (usually around 100 namometers in diameter) can enter into the human body through a very minor "defect" of the skin.

In response to the increased risk of exposure of health-care workers to the HIV, the virus causing AIDS, the Centers for Disease Control of the Public Health Service of the United States Department of Health and Human Services has made certain recommendations for the prevention of HIV transmission in health-care settings. See, Supplement, *Morbidity and Mortality Weekly Report*, Volume 36, No. 2s, Aug. 21, 1987. Among these recommendations is that gloves be worn during the administration of injections to patients or during the drawing of blood from patients. During these medical procedures, it is more than likely that the skin of a health-care worker will get in direct contact with the blood or body fluids of a patient. Wearing examination or surgical gloves provides a barrier to prevent the direct exposure of the skin of the health-care worker to the blood or other body fluids of the patient.

Unfortunately, there are certain drawbacks in wearing gloves while giving injections to patients or while withdrawing blood from patients.

Low cost plastic examination gloves are provided in essentially three sizes. More often than not, they very poorly fit the hands and fingers of a health-care worker. These low cost examination gloves usually have pockets or ridges of excess glove material lying over finger surfaces. The more expensive surgical quality latex gloves usually fit better, but are nevertheless slippery. Moreover, a large number of gloves have process related defects which include small leaks permeable to tiny viruses. Defects in gloves may also include intrinsic weak spots which will develop into leaks while the gloves are being worn and under handling stress. Finger nails, rings, and needle points, among other objects, can unknowingly puncture gloves, creating holes permeable to infectious agents.

Furthermore, the wearing of gloves during injection or venipuncture procedures may compromise the manual dexterity, or "feel," required for the procedure. The loss of manual dexterity during these procedures could lead to an increase in the incidence of needlesticks to the health care worker. Additionally, the decrease of manual dexterity, or the loss of "feel," by a health-care worker could compromise the finesse of touch required in minimizing the pain and discomfort for the patient receiving the injection or venipuncture.

It is a routine procedure to apply an adhesive backed bandage to skin puncture after an injection or a venipuncture procedure. This routine practice poses another problem to the wearer of gloves during a procedure, namely, the invariable stick of adhesive bandages or tape to the gloves. It is virtually impossible to remove an adhesive bandage that has stuck onto a glove without tearing it.

The cost of disposable gloves is not negligible. The time spent in donning and removing them is also costly. All these costs will ultimately contribute to the increase health care cost. The ratio of unit cost of a glove to a sponge or a wipe is approximately 5 to 1.

It is also a routine medical procedure to swab or wipe the skin puncture site with an absorbent sponge, typically of woven cotton, that has been saturated with an aqueous alcohol solution, usually a 70% solution of isopropyl alcohol. This swabbing or wiping is to prevent the entrance of pathogenic or infection agents to the body through these sites. After an injection or venipuncture procedure, an absorbent sponge is used to apply pressure to the skin puncture site to control bleeding.

As discussed above, the Centers for Disease Control has recommended wearing latex or synthetic polymer rubber gloves by health-care workers during the administration of an injection to a patient, or during the withdrawing of blood samples from a patient. The purpose of wearing gloves is to provide a barrier between the fingers and hand of the health-care worker and the patient's body fluids during swabbing, wiping or applying pressure to the skin puncture site. The latex or synthetic polymer rubber materials used in glove manufacture are impermeable to most infectous agents, provided that there are no leaks or other defects in the gloves.

Additionally, compliance is an issue to be considered. Use of gloves by health-care workers may be perceived by the patient as identification with a high risk group having an incurable disease. Additionally, procedural difficulties caused by the wearing of gloves may make health-care workers reluctant to wear them.

The medical sponges or wipes commonly used to swab or wipe the skin punctures have no built in impermeable barrier. Consequently, blood and other body fluids can easily pass through such porous sponges or wipes by capillary action or osmosis. Any infectious agents that might be present in the blood or other body fluids will likewise be carried along and will permeate such sponges or wipes. In view of the fact that sponges or wipes routinely used in wiping body fluids and cleansing skin puncture sites are "leaky," it is sensible for a health-care worker to wear gloves when administering an injection or performing a venipuncture procedure.

Because of their small sizes, infectious agents, such as viruses which may be present in the blood or body fluid, can, by means of capillary action pass through regular sponges or wipes very easily. The isopropyl alcohol solution used in conjunction with sponges or wipes does not necessarily achieve a total kill of all infectious agents that might be present in the blood absorbed into the sponges or wipes. In short, for total protection of both the health-care worker and the patient, a barrier that is impermeable to infectious agents must be interposed between the fingers and hands of the health-care worker and the blood and other body fluids of a patient.

In view of the fact that wearing of gloves poses many problems, it is highly desirable to have medical sponges or wipes with a barrier that is impermeable to infectious agents such as viruses. It is also desirable to have such a barrier that will prevent the seepage of blood or body fluids from the side that is in direct contact with such fluids to the opposite side that is being held by the user's bare fingers. Of course, medical sponges or wipes with a barrier impermeable to infectious agents can be used in conjunction with gloves. The "nonleaky" yet disposable sponges or wipes will offer an additional protection for both the glove-wearing health-care worker and the patient. After all, the gloves being worn could have leaks due to manufacturing imperfections or could have leaks developed during use due to abrasion or puncture.

It is toward such goals that the present invention is directed.

SUMMARY OF THE INVENTION

The present invention pertains to laminated medical sponge or wipe having one surface of an absorbent layer laminated or secured to at least one side of a thin and flexible sheet, having a top side and a bottom side, of barrier which is impermeable to infectious agents. The two sides are on opposite faces. The layer of absorbent material is of a smaller area than the impermeable sheet and is spaced inwardly from the entire peripheral edges of the impermeable sheet providing a peripheral rim or space of the impermeable sheet alone so that no body fluid can migrate or travel from one side of the sponge or wipe to the opposite side. The surrounding rim, being non-wettable, will prevent the migration of any body fluid, and any infectious agents that may be present therein, from one side of the sponge or wipe to the opposite side, around the peripheral edges of the impermeable sheet.

The impermeable sheet is also nonwettable by water, and is not soluble in water, blood, body fluids or solutions of antiseptic. During the use of this laminated medical sponge or wipe, this thin sheet of barrier creates a barricade between the skin of a health-care worker and any infectious agents that might be present in the blood or other body fluids of a patient.

The surrounding rim could be further surrounded by an integral peripheral ridge on at least one side of the sponge or wipe. Thus, the peripheral ridge and edges of the layer of absorbent material from an outlying moat, of impermeable sheet alone, that completely surrounds edges of the layer of absorbent material. The surrounding rim, the outlying moat and the peripheral ridge, all being nonwettable, are designed to prevent the seepage or migration of blood or other body fluids from one side of the laminated sponge or wipe to the opposite side through edges of the impermeable sheet.

BRIEF DESCRIPTION OF THE DRAWINGS

For a more complete understanding of the present invention and for further objects and advantages thereof, reference may now be had to the following description taken in conjunction with the accompanying drawings in which.

DETAILED DESCRIPTION

Figures 1, 2:
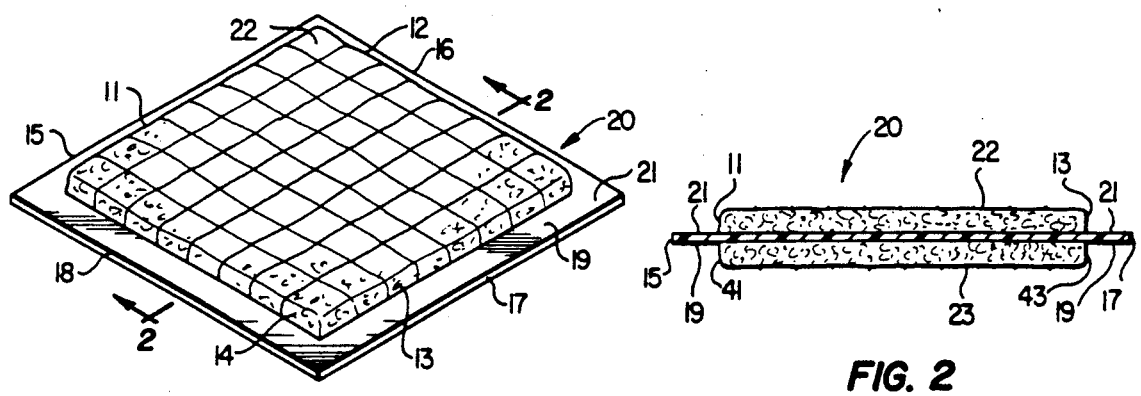
FIG. 1 is a perspective view of one embodiment of the laminated medical sponge constructed in accordance with the principles of the present invention.
FIG. 2 is an enlarged side-elevational, cross-sectional view of the laminated medical sponge taken along line 2—2 of FIG. 1.

The disposable laminated medical sponges or wipes of the present invention are constructed by laminating, securing, or cementing, a layer of porous absorbent material to at least one side of an impermeable sheet. In the trade, the terms "sponges" and "wipes" are used interchangeably. These laminated medical sponges or wipes are sterilizable and can be available either in a dry condition or in a moistened condition. Under moistened conditions, they are typically soaked in an antiseptic solution. The terms "alcohol soaked" or "alcohol prep" denote that the sponges are soaked in a solution of 70% of isopropyl alcohol.

The term "sheet" as used herein denotes a planar sheet which contains two opposite sides, one top and one bottom and four peripheral edges. The top and the bottom sides make up the two planar sides. The term "impermeable sheet" is used herein to denote a thin and flexible polymeric plastic sheet which is impervious or impermeable to any infectious virus or agent. "Flexible" refers to materials which are compliant and which readily conform to any external stress. The sheet is also not wettable by water and is insoluble in water, in body fluids, or in solutions of common antiseptic, such as a solution of 70% of isopropyl alcohol.

Solely laminating an impermeable sheet to a layer of absorbent will not totally prevent the seepage of blood or body fluids of a patient from one side of the laminated medical sponge or wipe to the other side. The reason is that when the peripheral edges of the impermeable sheet run abut and contiguous to the peripheral edges of the absorbent material, the blood or body fluid absorbed on the absorbent material can and will seep, wick or migrate around the edges and reach the opposite side of the sponge or wipe. To prevent this migration of blood or body fluids, the present invention purposely adopts a layer of absorbent material that has a size or an area that is smaller than that of the impermeable sheet. The peripheral edges of the layer absorbent material are then spaced inwardly away from the entire peripheral edges of said impermeable sheet. This arrangement provides a surrounding rim of the impermeable sheet alone which is also nonwettable by water and, thus, prevents the lateral spreading of blood or other body fluid. This rim can totally surround the peripheral edges of the layer of absorbent material. The function of this surrounding rim is to prevent the seepage or migration of fluids, through and around peripheral edges of the impermeable sheet, from the side in contact with blood or body fluids to the opposite side which is being held by the fingers of a health-care worker. Hence, any viruses or infectious agents that might be present in the blood or other body fluids will be confined to only one side or surface of the laminated medical sponge. Consequently, the bare or glove-covered skin of a health-care worker will not contact any viruses or infectious agents that might be present in the blood or other body fluids of a patient. Similarly, any infectious agents from the skin of a health-care worker will not be able to contaminate the skin puncture sites of the patient.

This thin impermeable sheet can be further reinforced on the periphery with an integral peripheral ridge around edges on at least one side of the impermeable sheet. This peripheral ridge could also be constructed on both the top and the bottom sides of the impermeable sheet. Adding a peripheral ridge creates a surrounding moat between the peripheral ridge and the entire peripheral edges of the layer of absorbent material that is cemented or secured onto the impermeable sheet. The moat, of the material of the impermeable sheet only, completely surrounds edges of the layer of absorbent material. This moat provides an additional trapping barrier so that blood or body fluids on one side of the sponge will not travel or migrate, through and around edges of the impermeable sheet to the opposite side that is being held by the fingers of a health-care worker. The peripheral ridges could be laminated, secured, or cemented onto the underlying impermeable sheet. Alternatively, the underlying impermeable sheet could be folded on the edges to create the peripheral ridge. The peripheral ridge could be made of similar material as the underlying impermeable sheet, or it could be made of other polymeric material. The peripheral ridge will help to prevent the collapse of the nonwettable periphery of the impermeable sheet. The thickness and width of the peripheral ridge, however, must not be of such magnitude that the resulting ridge will substantially impair the flexibility of the whole laminated medical sponge. The ridge should be made out of polymeric material that is nonwettable by water, impermeable to virus or infectious agent, and also insoluble in blood, in other body fluids, or in solutions of common antiseptic.

Typical flexible impermeable sheets are the synthetic resin films. These resin films include polyolefins and polyvinyl copolymers, such as polyethylene, polypropylene, polybutylene, polyvinyl acetate, polyvinyl chloride, polyvinylchloride-vinylidene chloride and the like. The thickness of the impermeable sheets is from about 0.5 mil to about 15 mils. The preferred thickness is from about 1.5 mils to about 5 mils. These impermeable sheets are flexible and have strength characteristics sufficient to resist tearing and piercing under normal manufacturing and handling stresses. These low cost sheets are nonwettable by water, can be sterilized and can be colored.

Typically, a laminated medical sponge or wipe will have the overall dimension of approximately 2"×2", that is, the impermeable sheet has an area of 2"×2". The layer of absorbent material typically has the dimension of about 1.5"×1.5". When a layer of this size of absorbent material is centrally positioned onto the impermeable layer, the laminated medical sponge or wipe will have a surrounding rim, consisting of the impermeable sheet alone, with a width of about ¼". The 2"×2" laminated medical sponge or wipe is the normal size used in applying pressure or in wiping blood or other body fluids from the skin puncture or needlestick sites of a patient after the administration of an injection or a venipuncture procedure. Of course, it is also possible to adopt various different sizes and shapes, such as rectangular, circular, oval, or a combination of such shapes, for the laminated medical sponge or wipes. Similarly, sizes and shapes of the layer of absorbent material secured to the impermeable sheet could also vary according to accepted practice in the medical art, as long as there is a surrounding rim or area of the impermeable sheet alone that completely surrounds edges of the layer of absorbent material.

The layer of absorbent material one surface of which is secured or lamented onto the impermeable sheet is porous and can be made of gauze cotton, prepared cotton, open-meshed cloth of varying degrees of fineness, synthetic fibers, or foamed polymer such as polyurethane. This layer typically maintains its strength when moistened. The thickness of the felted absorbent material can range from about 1/64 inch to about ⅛ inch. Typically, the thickness of the woven absorbent material can range from about 7/32 inch to ¼ inch for a 4"×4" of laminated sponge. For a smaller size sponge or wipe, such as the one with an overall dimension of 2"×2", typical thickness of the woven absorbent material is from about 3/64 inch to ⅛ inch.

The layer of absorbent material could be secured either on one side or on both sides of the impermeable sheet. Layers of absorbent material could be of equal thickness, but could also be of unequal thickness. Ordinarily, one layer of absorbent material will provide a nonslip surface for grasping with the fingers of a health-care worker. This surface is termed the "grasping layer." If needs be, the grasping layer does not have to have a full thickness of the absorbent material, as long as the grasping layer can provide a textured, nonslippery gripping surface. The other layer is then used to contact the patient's skin or body and to apply pressure or apply antiseptics to the patient's body. This layer is also used to wipe blood or other body fluids from the patient. This latter layer is termed the "wiping layer." The wiping layer will need the full thickness of the absorbent material. It is essential that the area or size of the layer of absorbent material is smaller than that of the underlying impermeable sheet and is secured away from the periphery of said sheet. It is not essential that the layer of absorbent material be centrally located on one side of the impermeable sheet. As discussed above, the main reason of spacing peripheral edges of the layer of absorbent material inwardly away from edges of the impermeable sheet is to create a surrounding area, space or rim between all edges of the absorbent material and all edges of the impermeable sheet. This surrounding rim will prevent seepage of blood or body fluids from the wiping surface to the holding surface through and over edges of the impermeable sheet. As discussed above, the impermeable sheet could also be reinforced with an integral peripheral ridge on either side of the impermeable sheet or on both the top and bottom sides of the impermeable sheet. Accordingly, either the grasping surface or the wiping surface, or both, could be surrounded by a peripheral ridge and the resultant moat. The ridge can have a thickness in the range of about 0.5 mils to about 10 mils. The width of the ridge interposing on the side of the impermeable sheet can range from about 1/16th to about ⅛th of an inch, thus, providing a peripheral moat with a width of about ⅛th to about 3/16th of an inch.

Depending on the material used for the impermeable sheet, different methods of securing or lamenting the layer of absorbent material can be used. The securing of the impermeable sheet and the layer of the absorbent material can be accomplished by standard techniques well known in the art of adhesives. To achieve a good bonding, it is a common practice to first degrease or rinse the adherent surface of the impermeable sheet by a organic solvent such as acetone or methyl ethyl acetone. The degreasing will prepare the surface suitable for bonding.

The common methods of joining polyolefins are thermal sealing and bonding, friction joining and vibrational welding such as ultrasonic assembly. See, *Encyclopedia of Polymer Science and Technology, Plastics, Resins, Rubbers, Fibers*. Vol. 16, 1967.

A typical ultrasonic welder is designed to deliver vibrations at a fixed frequency (usually in the 15 kHz. to 75 kHz. range) into the properly designed set of layers. The rapid agitation of the joint area under pressure creates frictional heat to melt the polymeric material in a fraction of a second. As the joint area melts, friction is reduced by the lubrication of the molten flowing polymeric material. The ultrasonic welder employs a power supply with an on-demand power output in the range of 1000 w, a pneumatic press which includes a piezoelectric converter to create the ultrasonic vibrations, programming controls, a ultrasonic welder employs a power supply with an on-demand power output in the range of 1000 w, a pneumatic press which includes a piezoelectric converter to create the ultrasonic vibrations, programming controls, a booster horn to amplify or deamplify the intensity of the vibrations, and a horn made of titanium to fit the assembly. The horn, in intimate contact and under pressure with one of the layers to be welded, transmits the ultrasonic vibrations through that part to the joint interface. Friction and high-frequency stress heat and melt the touching surfaces and the molten plastic flows and wet the parts to be joint. Pressure is maintained for a few seconds after the ultrasonic vibrations are delivered so that the joint has had time to resolidify. R. L. Babin, *Ultrasonic Assembly*, in Modern Plastics Encyclopedia, Vol. 63, Number 10A, pp. 365-370, October, 1986.

Because the preferred absorbent materials are porous, capable of absorbing in it liquified polymer, and, at the same time, the evaporation of solvent or vapor trapped in it, most of the standard joining methods using adhesives with or without solvents can be used. A preferred method to join the impermeable sheet to the layer of absorbent material is to extrude or roll a thin coat of any molten polyolefin, such as polyethylene, polypropylene or polybutylene, onto the adherent side of the impermeable sheet. S. M. Weiss, *Extrusion Coating and Lamenating*, in Modern Plastics Encyclopedia, Vol. 63, Number 10A, pp. 203-205, October, 1986. The layer of absorbent material is then applied contiguously to this adherent side and pressed together before solidification. Instead of applying a thin coat of polyolefin by extrusion, the standard rolling technique of direct gravure can be used to print the thin coat to selected areas of the adherent side of the impermeable sheet. S. J. Iwanski, *Roll Coating*, in Modern Plastics Encyclopedia, Vol. 63, Number 10A, pp. 205-206, October, 1986. The amount of the molten polyolefin used can vary depending on different factors. The range, however, can be broadly stated as from about 2% to about 20% of the weight of the impermeable sheet used. The molten polyolefin absorbed on the porous absorbent material will anchor to the impermeable sheet and, when cooled, will bind the layer of absorbent material and the impermeable sheet together. The adherent side of the porous material can also be precoated with polymer via deposition of powered polymer or extrusion or rolling of molten polymer.

Alternatively, solid powder polyolefins can be dispersed on the bonding side of the impermeable sheet in a thickness of from about 2 to about 10 mils. The layer of the absorbent material is then placed on top of the powder and the two are then subjected to high pressure heat seal with a heated bar sealer at a temperature sufficient to melt the polymer present on both sides of the absorbent layer-film interface, maintained at about 90° to 150° C. for polyethylene for about 0.05 to 5 seconds under a pressure of about 100-800 lb/in². absorbent layer. This adherent side of the absorbent layer can then be bonded to the impermeable sheet preferably by the standard thermal sealing method. See, *Modern Plastics Encyclopedia*, Volume 63, Number 10A, pp. 350-370, October 1986.

If both the impermeable sheet and the peripheral ridge are made of polyolefin, they can be bonded onto one another by the standard direct thermal or frictional methods discussed above.

Preferably, the pre-cut ridge is contiguously placed onto the impermeable sheet. The resulting sheet is then subjected to standard thermal sealing with a heated bar. A metal bar incorporating thermostatically controlled resistance elements presses the pre-cut ridge and the impermeable sheet against a second bar, which is not heated and is covered with a resilient layer of silicone rubber or other heat-resistant elastomer. Operable conditions are from about 0.05 seconds to about 5 seconds of dwell time at a temperature range at the interface between about 90° C. and about 150° C. while the pressure is kept from about 100 to about 800 lb/in².

As discussed above, the impermeable sheet can also be made of polyvinyl copolymers, such as polyvinyl acetate, polyvinyl chloride, polyvinylchloride-vinylidene chloride and the like. The chlorinate polyvinyl copolymers are highly resistant to exposure to either water or alcoholic solutions. Hence, for alcohol soaked or alcohol prep laminated medical sponges or wipes, the use of chlorinated polyvinyl copolymers as the impermeable sheet is preferred.

Chlorinated polyvinyl copolymers can be bonded by hot gas welding or solvent cementing. *Encyclopedia of Polymer Science and Technology, Plastics, Resins, Rubbers, Fibers.* Vol. 14, pp. 434–52, 1971. Solvent cementing is a preferred method over the hot gas welding method. All surfaces to be joined must be thoroughly cleaned and rinsed with a solvent such a methyl ethyl ketone or carbon tetrachloride before the cement is applied to the dry adherent surface. The cement used is typically a concentrated solution of chlorinated polyvinyl copolymers in a suitable solvent such as tetrahydrofuran. Such a cement usually contains about 2–40% by weight of the chlorinated polyvinyl copolymers in tetrahydrofuran. The amount of this cement used can vary depending on different factors. The range, however, can be broadly stated as from about 2% to about 20% of the weight of the impermeable sheet used.

Preferably, the chlorinated polyvinyl copolymer dissolved in an appropriate solvent is sprayed through a stencil or printed by the standard silk screening technique onto the adherent side of the impermeable sheet. J. Shields, *Adhesive Handbook*, 3rd ed. chapter 6, 1986. Before the solvent is evaporated, a layer of absorbent materials is applied contiguously onto the adherent side under pressure. The porous absorbent material will absorb the cement which will provide a binding anchor to the impermeable sheet. Any solvent trapped in the porous material will evaporate through the pores of the absorbent material.

Preferably, the peripheral ridge, also of chlorinated polyvinyl copolymers, can be secured along peripheral edges of the impermeable sheet by thermal, friction or ultrasonic means as discussed above.

Alternatively, one of the several cements or glues such as a polychloroprene contact cement or acetonitrile rubber is used. Typically, a solution of about 10–25 weight percent of polychoroprene rubber plus additives in toluene is used. The solution of polychoroprene is applied onto peripheral edges of both the impermeable sheet and the pre-cut peripheral ridge by the standard silk screening technique as discussed above. After drying, the pre-cut peripheral ridge is adhered contiguously to the peripheral edges by holding them at about 70°–90° C. for 10–30 minutes at a holding pressure of about 45–65 lb/in$^2$. J. Shields, *Adhesive Handbook*, 3rd ed. pp. 65–66, 1986. The amount of polychloroprene solution can vary depending on different factors. The range, however, can be broadly stated as from about 0.5% to about 10% of the weight of the impermeable sheet.

Referring first to FIG. 1, there is shown a diagrammatic, schematic representation of a laminated medical sponge or wipe constructed in accordance with the principles of the present invention. What is visible in the diagram is the top side of the laminated medical sponge 20. The bottom side of the laminated medical sponge 20 is obscured by the top side. The bottom side of the laminated medical sponge 20 could be laminated with another layer of absorbent material or with a layer of textured gripping surface. Alternatively, the bottom side may simply be bare, with no additional layer of absorbent material or textured gripping surface.

The numeral 20 designates the laminated medical sponge. A layer of absorbent material 22 is secured onto one side, the top side, of the impermeable sheet 19. Fluids, viruses or any other infectious agents cannot permeate this impermeable sheet 19. The impermeable sheet 19 can be made of thin, flexible polymeric plastic material, such as polyolefins or polyvinyl copolymers. This impermeable sheet 19 should be impermeable to the smallest viruses. It should also be nonwettable by water, and not dissolvable by body fluids or solutions of antiseptic.

The diagram shows that the layer of absorbent material 22 is of a smaller area than the underlying impermeable sheet 19. Peripheral edges 11, 12, 13 and 14 of layer 22 are spaced inwardly from p peripheral edges 15, 16, 17 and 18 of said sheet 19. Hence, there is a resultant area or rim 21 completely surrounding the peripheral edges of the layer of absorbent material 22. This surrounding rim consists of the impermeable sheet alone. The layer of the absorbent material 22 does not have to be centrally secured, or cemented, to the top side of the impermeable sheet 19 as shown in the diagram. An essential feature is that there is a surrounding peripheral rim of 21 between four edges, 11, 12, 13, and 14, of the absorbent material 22 and the corresponding four edges, 15, 16, 17 and 18, of the impermeable sheet 19. This surrounding rim or area 21, being part of the impermeable sheet which is non-wettable by water, will act as an additional barrier to prevent the seepage or migration of blood or body fluids around peripheral edges of the impermeable sheet from one side of the medical sponge to the other side of the sponge, such as from the top side to the bottom side.

The layer of absorbent material 22 can be made of porous materials such as gauge, cotton, prepared cotton, open-meshed cloth of varying degrees of fineness, synthetic fibers or foamed polymer, such as polyurethane. This fiber should not disintegrate when moistened.

Figure 3:
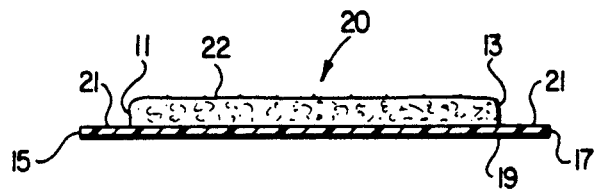
FIG. 3 is an enlarged side-elevational, cross-sectional view of an alternative embodiment of the laminated medical sponge taken along line 2—2 of FIG. 1.

FIG. 2 and FIG. 3 show enlarged side-elevational, cross-sectional views of two different embodiments of the laminated medical sponge 20 taken along line 2—2 of FIG. 1. FIG. 2 shows one embodiment in which there are two layers of absorbent material secured onto the impermeable sheet 19: a top layer of absorbent material 22 secured onto the top side of the laminated medical sponge 20, and a bottom layer of absorbent material 23 secured onto the bottom side of the laminated medical sponge 20. In this embodiment, one of the two absorbent layers, either 22 or 23, can be used as the "wiping layer" to wipe the blood or body fluid from a patient. This "wiping layer" is also the "contact layer" used to apply antiseptic or pressure onto the body of a patient. The other layer then will be used as the "grasping layer" to be grasped by the fingers of a health-care worker. Since the wiping layer and the grasping layer are separated by an impermeable sheet 19, no viruses or infectious agents can travel from one surface, such as 22, to the other surface, such as 23. As can be seen from FIG. 2, the impermeable sheet 19 also extends beyond all edges, 11, 13, 41, and 43, of both the top layer of absorbent material 22 and the bottom layer of absorbent material 23. The surrounding rim or area 21, being part of the same nonwettable material of the impermeable sheet 19, will not permit the flow or seepage of blood or other body fluids through and over edge 15 or 17 from one layer or surface, such as 22, to the opposite layer or surface, such as 23. Accordingly, any viruses or infectious agents that may be present in the blood or other body fluids will be confined to only one layer or surface of the laminated medical sponge. Because of this confinement, the skin of a health-care worker will not be exposed to the blood or other body fluids from a patient, hence the health-care worker will be spared the risk of getting contaminated with the viruses or other infectious agents from the patient. The impermeable sheet 19 laminated to layers of absorbent material, 22 and 23, will also provide a barrier to prevent the passage of any infectious agents from an infected health-care worker to the skin puncture sites of the patient. It should be noted that the top layer of absorbent material 22 does not have to be of equal thickness, or even of similar material, as of the bottom layer of absorbent material 23.

FIG. 3 shows that there is only one layer of absorbent material 22 secured or cemented onto one side of the impermeable sheet 19. This layer 22 will be used as the "wiping layer" to wipe blood or other body fluids from a patient. The other side, having no absorbent material, will be used as the "gripping layer" or "gripping surface." This surface may be textured or roughened to ensure gripping. There is still the surrounding rim or area 21 separating edges 11 and 13 of the absorbent material 22 from edges 15 and 17 of the impermeable sheet 19. This surrounding rim 21 is part of the same nonwettable material of the impermeable sheet. This surrounding rim 21 is to ensure that no blood or body fluids can migrate from the "wiping layer" to the "gripping layer" over edges of the impermeable sheet.

Figures 4, 5:
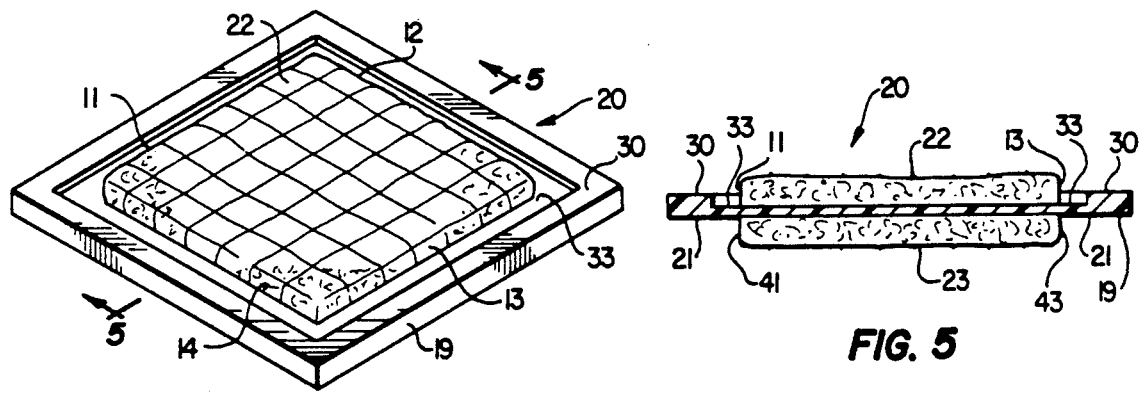
FIG. 4 is a perspective view of an alternative embodiment of the laminated medical sponge constructed in accordance with the principles of the present invention.
FIG. 5 is an enlarged side-elevational, cross-sectional view of the laminated medical sponge taken along line 5—5 of FIG. 4.

Referring now to FIG. 4, there is shown a perspective view of an alternative embodiment of the laminated medical sponge constructed in accordance with the principles of the present invention. Again, what is visible in the diagram is the top side of the laminated medical sponge 20. The bottom side of the laminated medical sponge 20 is obscured by the top side. The bottom side of the laminated medical sponge 20 could be laminated with another layer of absorbent material or with a layer of textured gripping surface. Alternatively, the bottom side may simply be bare, with no additional layer of absorbent material or textured gripping surface.

The layer of absorbent material 22 can be made of porous materials such as gauge, cotton, prepared cotton, open-meshed cloth of varying degrees of fineness, synthetic fibers, or foamed polymer. The impermeable sheet 19 can be made of thin, flexible polymeric plastic material. It is essential that this impermeable sheet 19 should be impermeable to the smallest viruses. The impermeable sheet 19 should also be nonwettable by water, and not dissolvable by body fluids or solutions of antiseptic.

Still referring to FIG. 4, the numeral 20 designates the laminated medical sponge. A layer of absorbent material 22 is secured onto one side, the top side, of the impermeable sheet 19. As discussed above, no viruses or any other infectious agents can permeate this impermeable sheet 19. The diagram shows that the layer of absorbent material 22 is of a smaller area than the underlying impermeable sheet 19 and is spaced inwardly from the periphery of said sheet 19. Moreover, the diagram shows a top integral surrounding ridge 30 surrounding the entire upper periphery of the impermeable sheet 19. Hence, a resultant moat 33 is formed around edges 11, 12, 13, and 14 of the layer of the absorbent material 22. The resultant moat is made up of the impermeable sheet alone. The impermeable sheet is, as discussed above, nonwettable by water. The layer of the absorbent material 22 does not have to be centrally secured, or cemented, to the top side of the impermeable sheet 19 as shown in the diagram. The essential feature is that there is a surrounding moat 33 between four edges, 11, 12, 13, and 14 of the absorbent material 22 and the top integral peripheral ridge 30. This moat will act as an additional trapping barrier to prevent the seepage of blood or body fluids from one side of the medical sponge 20 to the other side of the sponge 20, such as from the top side to the bottom side, over peripheral edges of the impermeable sheet.

The top integral peripheral ridge can be secured, laminated or cemented onto the underlying impermeable sheet 19. Alternatively, the underlying impermeable sheet could be folded on all edges to create the surrounding ridge 30. The top integral surrounding ridge could be made of similar material as the underlying impermeable sheet, or of any other polymeric material. Preferably, this top integral peripheral ridge 30 should also be nonwettable by water. This ridge 30 not only creates an additional barrier for the seepage of blood or other body fluids but also reinforces the underlying impermeable sheet 19 so that the periphery of the impermeable sheet is not easily collapsible. However, this ridge 30 should not be too thick or too wide as to hinder the flexibility of the medical sponge 20. The surrounding ridge 30 should be made of material that is insoluble in blood, in other body fluids, or in solutions of common antiseptic. The surrounding ridge 30 should be also nonwettable by water.

Figure 6:
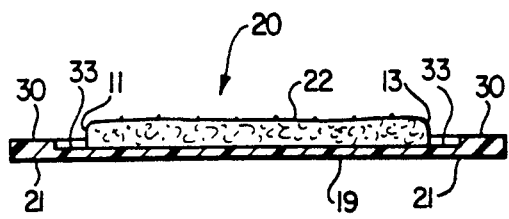
FIG. 6 is an enlarged side-elevational, cross-sectional view of an alternative embodiment of the laminated medical sponge taken along line 5—5 of FIG. 4.
Figure 7:
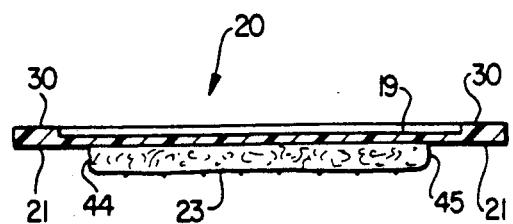
FIG. 7 is an enlarged side-elevational, cross-sectional view of another alternative embodiment of the laminated medical sponge taken along line 5—5 of FIG. 4.

FIGS. 5, 6, and 7 show enlarged side-elevational, cross-sectional views of three alternative embodiments of the laminated medical sponge 20 taken along line 5—5 of FIG. 4. All these alternative embodiments consist of a top integral surrounding ridge 30 on only one side, the top side, of the laminated medical sponge 20. FIG. 5 shows one embodiment in which there are two layers of absorbent material secured onto the impermeable sheet 19: a top layer of absorbent material 22 secured onto the top side of the laminated medical sponge 20 and a bottom layer of absorbent material 23 secured onto the bottom side of the laminated medical sponge 20. In this embodiment, either one of the two absorbent layers, 22 or 23, can be used as the "wiping layer" to wipe the blood or body fluid from a patient, or as the "contact layer" to apply antiseptic solutions. The other layer will then be used as the "grasping layer" to be grasped by the fingers of a health-care worker. Since the wiping layer and the grasping layer are separated by an impermeable sheet 19, no viruses or infectious agents can penetrate from one surface, such as 22, to the other surface, such as 23. As can be seen from FIG. 5, peripheral edges of the impermeable sheet 19 also extends beyond all edges, 11, 13, 41 and 43 of both the top layer 22 and the bottom layer 23 of absorbent material. The surrounding rim or area 21, being part of the same nonwettable material of the impermeable sheet 19, will prevent the flow or seepage of blood or other body fluids through edge 15 or 17 from one layer or surface, such as 22, to the other layer or surface, such as 23. Furthermore, the top moat 33, created between the top integral surrounding ridge 30 and edges 11 and 13 of the top layer of absorbent material 22, further functions as a trapping barrier for the migration of blood or any body fluids from one side of the sponge 20 to the other side of the sponge 20. Hence, blood or any body fluids present on the top layer of absorbent material 22 will be unable to travel to the bottom layer of absorbent material 23. Likewise, blood or any body fluids present on the bottom layer of absorbent material 23 cannot travel to the top layer of absorbent material 22. Hence, any viruses or infectious agents present in the blood or other body fluids will be confined to only one layer or surface of the laminated medical sponge. The presence of an impermeable sheet 19 together with the confinement of any infectious agents to only one side of the laminated medical sponge will prevent any possible cross-contamination or cross-infection between a patient and a health-care worker. It should be noted that the top layer of absorbent material 22 does not have to be of equal thickness, or even of similar material, as of the bottom layer of absorbent material 23.

FIG. 6 shows that there is only one layer of absorbent material 22 secured or cemented onto the top side of the impermeable sheet 19. This layer 22 will be used as the "wiping layer" to wipe blood or other body fluids from a patient. The opposite side, having no absorbent material, will be used as the "gripping layer" or "gripping surface." This surface can be textured or roughened for a better grip. There is still the surrounding rim or area 21 separating edges 11 and 13 of the absorbent material 22 from edges 15 and 17 of the impermeable sheet 19. Moreover, the top moat 33 surrounding edges 11 and 13 of the top layer of absorbent material 22 will trap any blood or body fluids overflowing from the top absorbent layer 22. Consequently, any viruses or infectious agents present in the blood or body fluids will be confined to only one side or surface of the laminated medical sponge 20, namely, the top layer of absorbent material 22. Such a confinement will spare the skin, or potentially defective gloves, of a health-care worker from being directly exposed to viruses or any other infectious agents from a patient. Of course, the presence of any barrier will also prevent a patient from being contaminated by an infected health-care worker.

FIG. 7 shows an enlarged side-elevational, cross-sectional view of another alternative embodiment of the laminated medical sponge 20 taken along line 5—5 of FIG. 4. Unlike the embodiment as shown in FIG. 6, here, the layer of absorbent material is secured or cemented to the bottom side of the medical sponge 20. The integral peripheral ridge 30 is situated on the top side of the laminated medical sponge 20. Obviously, the bottom layer of absorbent material 23 will be used as the "wiping layer." The top side of the impermeable sheet 19 will be used as the "grasping layer." Because of the presence of both the surrounding rim or area 21 and the top integral peripheral ridge 30, blood or body fluids from a patient absorbed by the layer 23 cannot migrate through and over edges of the impermeable sheet to the other side of the medical sponge where it is being grasped by a health-care worker. Consequently, viruses or other infectious agents are confined to the bottom layer of the absorbent material 23. This confinement will prevent the direct contact of the viruses or other infectious agents with the skin of the health-care worker, hence, reducing the risk of infecting the health-care worker with viruses or any other infectious agents. Similarly, the presence of a barrier will also spare a patient from being contaminated by an infected health-care worker.

Figure 8:
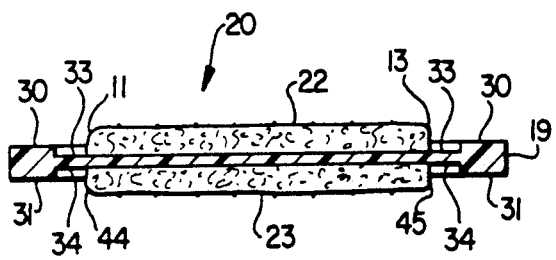
FIG. 8 is an enlarged side-elevational, cross-sectional view of yet another alternative embodiment of the laminated medical sponge taken along line 5—5 of FIG. 4.
Figure 9:
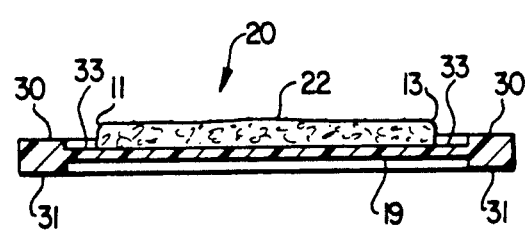
FIG. 9 is an enlarged side-elevational, cross-sectional view of still another alternative embodiment of the laminated medical sponge taken along line 5—5 of FIG. 4.

Referring now to FIGS. 8 and 9 where two other alternative embodiments of the laminated medical sponges taken along line 5—5 of FIG. 4 are shown. In these two alternative embodiments, the impermeable sheet is completely surrounded on both the top and the bottom sides along the periphery by a top integral peripheral ridge 30 and a bottom integral peripheral ridge 31, respectively. The embodiment as shown in FIG. 8 has two layers of absorbent material, one on the top side, 22, and the other on the bottom side, 23. The two layers of absorbent material 22 and 23 do not have to be of equal thickness, nor do they have to be made of similar material. Either layer can be used as the "wiping layer." If the two layers 22 and 23 are of unequal thickness, it is preferable to use the thicker of the two layers as the "wiping layer." Again, a top moat 33 separates the top peripheral ridge 30 from edges 11 and 13 of the top layer of absorbent material 22. This top moat 33 also surrounds the entire top layer of absorbent material 22. Likewise, a bottom moat 34 separates the edges 44 and 45 of the bottom layer of absorbent material 23 from the bottom integral peripheral ridge 31.

The embodiment as depicted in FIG. 9 has only a single layer of top absorbent material 22. By necessity, the top layer of absorbent material 22 will be used as the "wiping layer." Edges 11 and 13 of the absorbent layer 22 are separated from top integral peripheral ridge 30 by a top moat 33.

Similar to other alternative embodiments described above, either of the embodiment depicted in FIGS. 8 and 9 will confine blood or any body fluids from a patient to only the "wiping layer." The skin of a health-care worker will not be directly exposed to the blood or any body fluids from a patient. Consequently, a health-care worker using such a laminated medical sponge will not run the risk of being infected by viruses or any other infectious agents that might be present in the blood or other body fluids of a patient. Similarly, skin puncture sites on a patient will not run the risk of being contaminated by any infectious agents that might be present on the fingers of an infected health-care worker.

Figure 10:
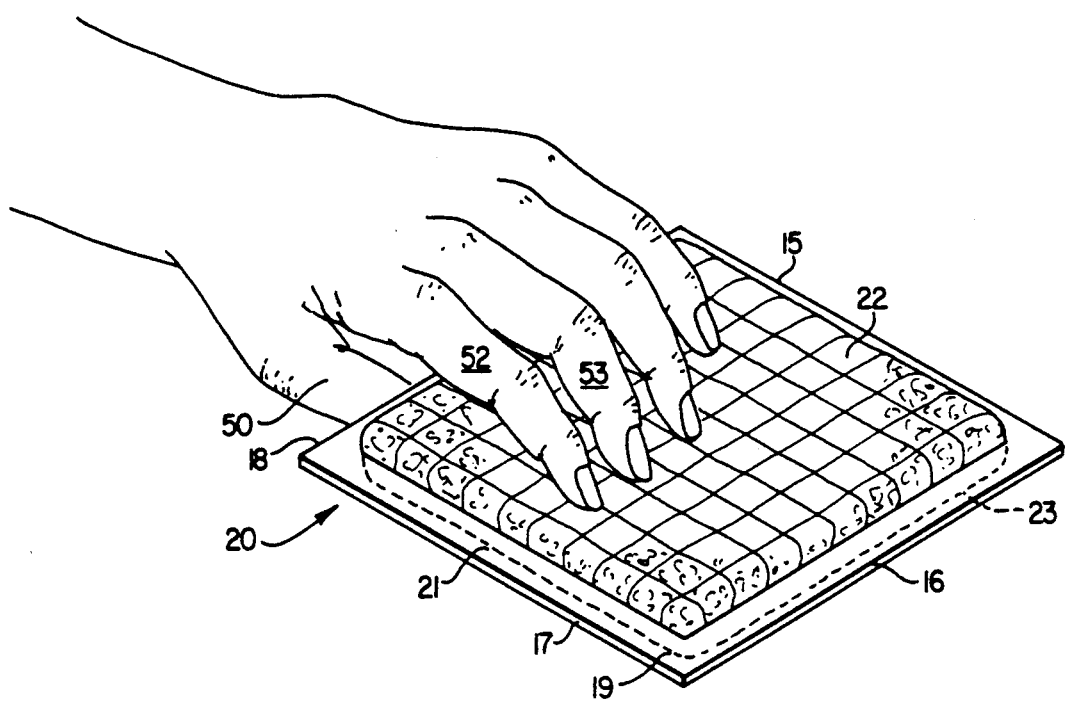
FIG. 10 is a diagram of one embodiment of the laminated medical sponge, constructed in accordance with the principles of the present invention, under use environment.

FIG. 10 is a diagram showing the actual use of one embodiment of the disposable laminated medical sponge, constructed according to the principles of the present invention. The diagram shows the thumb 50, second finger 51, and middle finger 52 of a health-care worker gripping the grasping layer 22 of the laminated medical sponge 20. Ordinarily, while using a conventional "leaky" sponge or wipe, the thumb of the health-care worker is in direct contact with the wiping area. In contrast, the proper way to use the present invention is to avoid having any part of the hand of a health-care worker touching the wiping layer. The impermeable sheet 19 has an area that is larger than either the grasping layer 22 or the wiping layer 23. Moreover, all peripheral edges of both the grasping layer 22 and the wiping layer 23 are spaced inwardly from edges 15, 16, 17, and 18 of the impermeable sheet 19 leaving a surrounding rim or area 21. The surrounding rim is part of nonwettable impermeable sheet. As such, this surrounding rim or area 21 will help to prevent the patient's blood or body fluids from seeping from the wiping layer 23 over edges 15, 16, 17 and 18 to the grasping layer 22. Consequently, blood and other body fluids of the patient are confined to the wiping layer 23. As a result of this confinement, the fingers, either bared or gloved, of the health-care worker are spared the risk of being directly exposed to any viruses or other infectious agents that might be present in the blood or other body fluids. Likewise, viruses or other infectious agents that might be present on the fingers of an infected health-care worker cannot contaminate the wiping layer 23, hence the patient is also spared the risk of getting contaminated by an infected health-care worker.

It is believed that the operation and construction the abovedescribed invention will be apparent from the foregoing description. While medical sponges with a barrier impermeable to infectious agents shown and described have been characterized as being preferred, it will be obvious that various changes and modifications may be made without departing from the spirit and scope of the invention as defined in the following claims.

What is claimed is:

1. A laminated medical sponge, comprising:

a thin and flexible sheet, having a top side and a bottom side, impermeable to infectious agents;

an integral peripheral ridge means on at least one side of said sheet and surrounding the entire peripheral edges of said sheet;

a first layer of absorbent material, having a top surface and a bottom surface and being of a smaller area than said sheet, one said surface of is secured on one side, the wiping side, of said sheet, and having the entire peripheral edges of said first layer spaced inwardly away from the entire said peripheral ridge of said sheet providing a surrounding moat of said sheet alone so that any liquid on said first layer of absorbent material cannot travel through said surrounding moat or wick around said peripheral ridge to reach the opposite side of said sheet adapted to be grasped by being gripped between one's fingers around the central region of said sheet; and a second layer of absorbent material, having a top surface and a bottom surface and being of a smaller area than said sheet, one said surface of is secured on the opposite side, the grasping side, of said sheet, and having the entire peripheral edges of said second layer spaced inwardly away from the entire said peripheral edges of said sheet providing a surrounding area of said sheet alone.

2. The laminated medical sponge as defined in claim 1 wherein said first and said second layers of absorbent material on the top and the bottom sides of said sheet are of unequal thickness.

3. The laminated medical sponge as defined in claim 1 wherein said first and said second layers of absorbent material on the top and the bottom sides of said sheet are of equal thickness.

4. A disposable article comprising:

a flexible fluid impervious sheet;

an integral peripheral ridge means located on said sheet and surrounding the entire peripheral edges of said sheet to prevent leakage or migration of fluids;

a layer of absorbent material having a surface area which is smaller than the surface area of said sheet, said layer of absorbent material being secured to one side of said sheet and spaced inwardly from said peripheral ridge means; and a second layer of absorbent material having a surface area which is smaller than the surface area of said sheet, said second layer of material being secured and extending from a second side of said sheet and spaced inwardly from said peripheral ridge means.

5. A disposable article comprising:

a flexible fluid impervious sheet;

an integral peripheral ridge means located on said sheet and surrounding the entire peripheral edges of said sheet to prevent leakage or migration of fluids;

a layer of absorbent material having a surface area which is smaller than the surface area of said sheet, said layer of absorbent material being secured to one side of said sheet and spaced inwardly from said peripheral ridge means; and a second layer of material having a surface area which is smaller than the surface area of said sheet, said second layer of material being secured and extending from a second side of said sheet and spaced inwardly from said peripheral edges of said sheet.

* * * * *

UNITED STATES PATENT AND TRADEMARK OFFICE
CERTIFICATE OF CORRECTION

PATENT NO. : 5,009,652

DATED : April 23, 1991

INVENTOR(S) : Cheryle I. Morgan and Millard M. Judy

It is certified that error appears in the above-identified patent and that said Letters Patent is hereby corrected as shown below:

On the title page, please insert item [73] Assignees: to read as follows:

--[73] Assignees: Allan Weinstein, Potomac, Maryland; Robert Weinstein, West Bloomfield, Michiagan--.

Signed and Sealed this

Third Day of November, 1992

*Attest:*

DOUGLAS B. COMER

*Attesting Officer*  *Acting Commissioner of Patents and Trademarks*